United States Patent [19]

Kanner et al.

[11] 4,400,526
[45] Aug. 23, 1983

[54] HYDROGEN BEARING SILYL CARBAMATES

[75] Inventors: Bernard Kanner, West Nyack; Curtis L. Schilling, Jr., Croton-On-Hudson; Steven P. Hopper, Mahopac, all of N.Y.

[73] Assignee: Union Carbide Corporation, Danbury, Conn.

[21] Appl. No.: 430,373

[22] Filed: Sep. 30, 1982

[51] Int. Cl.³ ............................................... C07F 7/10
[52] U.S. Cl. .................................................... 556/420
[58] Field of Search ........................................ 556/420

[56] References Cited

U.S. PATENT DOCUMENTS

| | | | |
|---|---|---|---|
| 3,284,485 | 11/1966 | Goossens | 556/420 X |
| 3,364,175 | 1/1968 | DiPaola | 556/420 X |
| 3,494,951 | 2/1970 | Berger | 556/420 |
| 3,715,371 | 2/1973 | Thomson | 556/420 X |
| 4,064,151 | 12/1977 | Hedaya et al. | 556/420 |
| 4,255,348 | 3/1981 | Herdle et al. | 556/410 |

FOREIGN PATENT DOCUMENTS

| | | | |
|---|---|---|---|
| 902628 | 6/1972 | Canada | 556/420 |
| 540869 | 12/1976 | U.S.S.R. | 556/420 |

OTHER PUBLICATIONS

J. Chem. Soc. (A) 1967 p. 362, Ebsworth et al.
J. Chem. Soc. (A) 1970 p. 279, Glidewell et al.

Primary Examiner—Paul F. Shaver
Attorney, Agent, or Firm—Paul W. Leuzzi, II

[57] ABSTRACT

A hydrogen bearing silyl carbamate of the general formula:

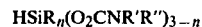

$HSiR_n(O_2CNR'R'')_{3-n}$ is synthesized from hydrogen bearing aminosilane and gaseous carbon dioxide. The resulting hydrogen bearing silyl carbamate is novel in the single hydrogen attached to the silyl carbamate and represents a major new compound for creating novel compositions of matter.

19 Claims, No Drawings

HYDROGEN BEARING SILYL CARBAMATES

BACKGROUND OF THE INVENTION

The instant invention relates to a novel silyl carbamate. More particularly, the novel carbamate contains only a single hydrogen bonded to the silicon atom and may be represented by the general formula:

$$HSiR_n(O_2CNR'R'')_{3-n}$$

The literature previously reported silylcarbamates bearing three (3) hydrogens. They are reported in J. Chem. Soc., A(1970) 279 by Gledewell and Rankin as derived from pyrrolidinosilane, diethylaminosilane and dimethylaminosilane. These compositions fail to suggest that single hydrogen bearing silyl carbamates can be prepared. Conversely, the literature previously reported silylcarbamates bearing three (3) hydrocarbon radicals but no silyl hydrogen linkage. Included are dimethylcarbamatotrimethylsilane, bis(dimethylcarbamato)dimethylsilane, and bis(diethylcarbamato)dimethylsilane. Bazant et al., Organosilicon Compounds, Vol. 1, Academic Press, New York, 1965. Again, these compositions fail to suggest that single hydrogen bearing silyl carbamates can be prepared.

Despite these known silyl carbamates bearing either three hydrogens or three hydrocarbon radicals, single hydrocarbon bearing silyl carbamates are unreported in the art. Single hydrogen bearing silyl amines are known in the art. Examples of such hydrogen bearing silyl amines are reported in U.S. Pat. No. 4,255,348 to Herdle and Kanner.

Insofar as the industry is forever seeking to develop new and useful compounds that possess the potential to open frontiers to new compositions of matter, new utilities and greater efficiencies, the discovery of single hydrogen bearing silyl carbamates represents a technical advance in the art. Furthermore, the reported showing of enhanced hydrosilation reactivity of these novel single hydrogen bearing silyl carbamates over single hydrogen bearing silyl amines opens up a whole new area of utility.

SUMMARY OF THE INVENTION

The instant invention provides novel hydrogen bearing silyl carbamates of the general formula:

$$HSiR_n(O_2CNR'R'')_{3-n}$$

wherein R is a saturated or unsaturated, substituted or unsubstituted, alkyl, aryl, alkoxy or dialkylamino radical containing from one to 12 carbon atoms inclusive, R' and R" are individually selected from the group consisting of saturated or unsaturated, substituted or unsubstituted alkyl or aryl hydrocarbon radicals containing from one to 12 carbon atoms inclusive and n has a value of from 0 to 2. The novel hydrogen bearing silyl carbamates are synthesized from hydrogen bearing aminosilanes and gaseous carbon dioxide. The resulting hydrogen bearing silyl carbamates is novel in the single hydrogen attached to the silyl carbamate and represents a major new compound for creating novel compositions of matter. Additionally, the novel hydrogen bearing silyl carbamates of the instant invention provide an improved route for hydrosilation reactions.

DETAILED DESCRIPTION OF THE INVENTION

In accordance with the present invention, there is provided a novel class hydrogen bearing silyl carbamates of the general formula I. These hydrogen bearing silyl carbamates are synthesized from the reaction of aminosilanes and gaseous carbon dioxide.

The aminosilanes considered suitable as a starting material for the present invention are of the general formula:

$$HSiR_n(NR'R'')_{3-n}$$

wherein R, R' and R" and N are all as previously defined. Aminosilanes of this type may be synthesized in accordance with the procedures set forth in Organosilicon Compounds. Vol. 1, Academic Press, New York, 1965. Tri(dimethylamino)silane in particular may be prepared in accordance with the procedures set forth in U.S. Pat. No. 4,255,348 issued Mar. 10, 1981 to Herdle and Kanner.

Illustrative of the silanes which may be converted to hydrogen bearing silyl carbamates include, but are not limited to, dimethylaminodimethylsilane, diethylaminodimethylsilane, methylethylaminodimethylsilane, ethylphenylaminodimethylsilane, diphenylaminodimethylsilane, dibenzylaminodimethylsilane, phenylbenzylaminodimethylsilane, benzylmethylaminodimethylsilane, bis-dimethylaminoethylsilane, bis-diethylaminoethylsilane, bis-methylethylaminoethylsilane, bis-ethylphenylaminomethylsilane, bis-methylethylaminoethylsilane, bis-ethylphenylaminomethylsilane, bis-diphenylaminomethylsilane, bis-dibenzylaminoethylsilane, bis-phenylmethylaminoethylsilane, bis-benzylethylaminomethylsilane, bis-dimethylaminophenylsilane, bis-diethylaminophenylsilane, bis-diethylaminobenzylsilane, bis-ethylpropylaminobenzylsilane, bis-diphenylaminoethylsilane, bis-dibenzylaminopropylsilane, bis-diphenylaminobutylsilane, bis-dibenzylaminoisopropylsilane, tris-dimethylaminosilane, tris-diethylaminosilane, tris-methylethylaminosilane, tris-ethylphenylaminosilane, tris-diphenylaminosilane, tris-dibenzylaminosilane, tris-phenylpropylaminosilane, tris-benzylpropylaminosilane, dicyclopentylaminodimethylsilane, cyclopentylmethylaminodimethylsilane, dicyclohexylaminodimethylsilane, cyclohexylmethylaminodimethylsilane, bis-dicyclopentylaminomethylsilane, bis-cyclopentylaminosilane, dicyclopentylaminodiphenylsilane, bis-dicyclopentylaminomethylsilane, tris-dicyclopentylaminosilane, cyclohexylmethylaminodimethylsilane, bis-cyclohexylaminomethylsilane, bis-cyclohexylphenylaminomethylsilane, tris-cyclo- hexylmethylaminosilane, tris(piperidino)silane, dimethylaminodiethoxysilane, diethylamino- dimethyoxysilane, bis-dimethylaminoethoxysilane, bis-diethylaminopropylpropoxysilane, propylaminodimethoxysilane, and the like.

The coreactant in the synthesis is gaseous carbon dioxide. The synthesis conditions under which the novel hydrogen bearing silyl carbamates are prepared are between a temperature of −20° C. to 150° C. and preferably from 0° to 50° C. Atmospheric pressure is recommended although other pressures may be employed with the corresponding alteration in temperature, time and yields. The synthesis time is generally from 10 minutes to up to 3 hours with one-half to an hour being preferred. The yields are relatively high and essentially quantitative. No significant side reactions have been observed. Catalysts are not necessary although they may be employed without adversely affecting the reaction. Molecular amounts used in the reaction are stoichiometric although in making triscarbamatosilane it is preferred to use an excess of carbon dioxide. The synthesis may be conducted with or without a solvent. When a solvent is desirable ethers such as diethylether or tetrahydrofuran may be employed or hydrocarbons such as hexane or toluene may be employed. It is careful that any solvent chosen does not react with either the starting materials or the product. The synthesis is usually carried out in an inert atmosphere such as nitrogen or argon. It is recommended that the atmosphere be dry in that moisture can lead to undesirable effects. As mentioned above the synthesis is usually carried out at ambient pressures but it can be carried out under a carbon dioxide pressure up to 150 psig.

The single hydrogen bearing silyl carbamate produced under these synthesis conditions is of the general formula:

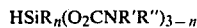
$$HSiR_n(O_2CNR'R'')_{3-n}$$

wherein R, R'R" and n are all as previously defined. Illustrative of the hydrogen bearing silyl carbamates that may be prepared include, but are not limited to, dimethylcarbamatodimethylsilane, ethylmethylcarbamatodimethylsilane, diphenylcarbamatodimethylsilane, dibenzylcarbamatodimethylsilane, bis-(dimethylcarbamato)methylsilane, bis-(diethylcarbamato)methylsilane, tris(dimethylcarbamato)silane, tris(diphenylcarbamato)silane, dimethylcarbamatodiethyoxysilane, diethylcarbamatodimethyoxysilane, bis-dimethylcarbamatomethoxysilane, bis-diethylcarbamatopropoxysilane, propylcarbamatodimethoxysilane, bis-dimethylcarbamatodimethylsilane, bis-dimethylaminodimethylcarbamatosilane, bis-piperidoincarbamatosilane, bis-diethylaminodiethylcarbamatosilane, and the like.

The novel hydrogen bearing silyl carbamates are deemed particularly useful due to the presence of a single hydrogen attached to the silyl carbamate. Although many of the utilities expected for this compound remain unexplored, it has surprisingly been found that this compound has great utility in the well known hydrosilation reaction. Although the corresponding aminosilanes, when reacted with a monomer in the presence of a platinum catalyst reacted in low yield, the novel hydrogen bearing silyl carbamates of the present invention, when reacted under the same conditions, successfully reacted in high yield to give the corresponding hydrosilation product. This surprising and unexpected result obtainable through employing the hydrogen bearing silyl carbamates clearly established the utility available to these compounds and the potential for other utilities to be discovered.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLE I

Preparation of Tris(dimethylcarbamato)silane

A 500 ml, round bottomed, three necked flask equipped with a magnetic stirring unit, carbon dioxide inlet tube and a reflux condenser topped with an argon inlet tube was flushed with argon. The flask was then charged with 53.2 gm (0.33 mole) of tris(dimethylamino)silane and 70 gm of reagent grade hexane. The flask and its contents were cooled with stirring under argon to ca. 5° C. by means of an external wet ice bath. A stream of dry carbon dioxide was introduced below the surface of the stirred reaction mixture. After about 15 minutes of carbon dioxide addition to the cooled, stirred reaction mixture, two phases were evident. White solid separate from the reaction mixture after ca. 20 minutes of carbon dioxide addition. The total addition time was three hours to insure that excess carbon dioxide had been added.

The reaction mixture was then filtered and the white solid was washed twice with fresh cold hexane. The solid thus isolated was dried in vacuo for three hours. The product, 82.6 gm (86%) was characterized as tris(-dimethylcarbamato)silane by the following data:
m.p. 80°(Dec.)
NMR (CCl$_4$ with internal (Me$_3$Si)$_2$O standard) 5.00, s, 1 H, SiH and 2.83 ppm, s, 18H, Me$_2$N—.
IR (nujol mull) 2270 cm$^{-1}$, Si-H, 1695 cm$^{-1}$, CO.
Anal. Calcd. for C$_9$H$_{19}$N$_3$O$_6$Si: C, 36.85; H, 6.53; N, 14.32; Si 9.57. Found: C, 36.56, H, 6.71; N, 14.27; Si, 9.53

EXAMPLE II

Preparation and Isolation of Bis(dimethylcarbamato)dimethylaminosilane

A 100 ml, round bottomed, three necked flask equipped with a magnetic stirring unit, thermometer, Dry Ice/acetone condenser topped with a nitrogen inlet and a carbon dioxide inlet system with a 5 mm opening (smaller openings tended to plug up with solids) was charged with 14.0 gm (87.0 mmole) of tris(dimethylamino)silane and 30 gm of reagent grade hexane. The carbon dioxide inlet tube extended as far to the bottom of the flask as possible. The reaction mixture was cooled in a wet ice bath to ca. 4° C. The carbon dioxide sparge was initiated and maintained at a rate of ca. 0.15 standard cubic foot of air per hour for 28 minutes. During this time, the temperature rose to and held at 9° C. At this time the sparging was stopped for ¾ hour. Thirteen minutes after the sparge was resumed at the same rate the reaction mixture became opaque with two distinct phases present. After an additional four minutes the carbon dioxide sparge was stopped. The reaction mixture had been sparged for a total of forty-five minutes at a rate of ca. 0.15 SCFH. Filtration of the reaction mixture through a coarse fritted disk yielded 3.67 gm (14%, all yields quoted as percent of silicon charged) of white crystalline tris(dimethylcarbamato)silane, (hereinafter called TRIS-CARB). The filtrate was cooled in a wet ice bath and a lower layer of opaque liquid, 5.3 gm. separated from the reaction mixture. The lower layer was removed by transfer pipet and examined nmr. The lower layer contained 1.8 gm (7%) of TRIS-CARB and 3.5 gm (16%) of bis(dimethylcarbamato)dimethylaminosilane, (hereinafter called BIS-CARB). The upper hexane layer was rotary evaporated to give 12.0 gm of crude product. Examination of this crude product by NMR indicated the presence 1.32 gm (6%) bis(dimethylamino)dimethylcarbamatosilane (hereinafter called MONO-CARB), 9.5 gm (44%) BIS-CARB and 1.1 gm (5) of TRIS-CARB. The isolated BIS-CARB was 75% pure and obtained in 44% overall yield based on silicon charged. A total of 92% of the silicon charged was accounted for by the products.

EXAMPLE III

Preparation of Bis(dimethylcarbamato)methylsilane

In a 50 ml round bottomed, three-necked flask fitted with magnetic stirrer, thermometer, condenser, $N_2$ valves, and carbon dioxide sparge tube there was placed 22.g of bis(dimethylamino) methylsilane. Carbon dioxide was passed through the system for 6 hours with a maximum temperature (reaction is exothermic) of 47°. VPC/NMR Analysis indicated quantitative conversion to biscarbamate. Attempted distillation resulted in decomposition of the biscarbamate, indicating this compound is thermally unstable.

EXAMPLE IV

Preparation of Bis(dimethylcarbamato)methylsilane

A round bottomed, three necked 50 ml flask equipped with a magnetic stirring unit, thermometer, sparge tube and a reflux condenser topped with a nitrogen inlet tube was flushed with nitrogen and charged with 21.8 gm (0.165 mole) of bis-N,N-dimethylaminomethylsilane. The carbon dioxide sparge was commenced and the temperature of the stirred reaction mixture was maintained at about room temperature by means of a wet ice bath periodically applied to balance the exotherm of the reaction. After about one and one quarter hours sparging it appeared that no further carbon dioxide was being absorbed by the reaction mixture. The carbon dioxide sparge was continued for an additional half hour to insure complete reaction. The clear, water white reaction mixture was transferred to a single necked flask and rotary evaporated at aspirator pressure for one and one half hours. The yield of the title compound was quantitative. The isolated product gave an unambiguous NMR spectrum with the proper integration as well as an infrared spectrum which contained absorptions at 2220 cm$^{-1}$ (Si-H) and 1670 cm$^{-1}$ (carbamate carbonyl).

EXAMPLE V

Carbon dioxide Insertion Reaction of Dimethylaminodimethylsilane

In a 50 ml 3 NRB$ flask fitted with magnetic stirrer, thermometer, condenser, $N_2$ valves, and carbon dioxide sparge tubes there was placed 24.3 g of dimethylaminodimethylsilane. Carbon dioxide flow was started and continued at a rate causing a slow exotherm from 25° to 70° C. in 80 minutes. Reaction was complete by VPC at 100 minutes. Vacuum distillation yield 29.1 g of dimethylcarbamatodimethylsilane, b.p. 50°-52°/17 mm, identified by NMR. The yield was 83.9%.

EXAMPLE VI

Reaction of Dimethylaminodiethylsilane With Vinylheptamethylcyclotetrasiloxane

In a typically fitted 25 ml apparatus there was combined 15.4 g of 92% vinylheptamethylcyclotetrasiloxane and chloroplatinic acid catalyst. The mixture was heated to 108°, then addition of 5.15 gm of dimethylaminodimethylsilane was begun. Addition was completed in one hour followed by refluxing 135° for an additional 1.5 hour. Vacuum distillation yielded 16.1% of dimethylaminodimethylsilylethylheptamethylcyclotetrasiloxane.

EXAMPLE VII

Reaction of Dimethylcarbamatodimethylsilane With Vinylheptamethylcyclotetrasiloxane In a typically fitted 50 ml apparatus were combined 13.3 g of dimethylcarbamatodimethylsilane and 28.0 g of vinylheptamethylcyclotetrasiloxane. Pt Catalyst solution (0.05 ml) was added at 22° and heat applied after a slow exotherm to 37°. After 2 hours (maximum temperature = 85°), reaction was complete by VPC. Distillation yielded 36.9 g (90.1%) of dimethylcarbamatodimethylsilylethylheptamethylcyclotetrasiloxane, b.p. 100°/0.08 mm, as identified by NMR.

We claim:

1. A compound selected from the group consisting of those compounds of the formula:

$$HSiR_n(O_2CNR'R'')_{3-n}$$

wherein R is a saturated or unreacted, substituted or unsubstituted alkyl, aryl, alkoxy or dialkylamino radical containing from one to twelve carbon atoms inclusive; R' and R'' are individually selected from the group consisting of saturated or unsaturated, substituted or unsubstituted alkyl or aryl hydrocarbon radicals containing from one to twelve carbon atoms inclusive; and n has a value of from 0 to 2.

2. The compound selected from the group consisting of those compounds set forth in claim 1 wherein, R, R' and R'' individually contain from one to six carbon atoms.

3. The compound selected from the group consisting of those compounds set forth in claim 2 wherein R, R' and R'' are individually alkyl radicals.

4. The compound selected from the group consisting of those compounds set forth in claim 3 wherein n=o.

5. The compound selected fro the group consisting of those compounds set forth in claim 3 wherein n=1.

6. The compound selected from the group consisting of those compounds set forth in claim 3 wherein n=2.

7. A compound selected from the group consisting of those compounds of the formula:

$$HSi(O_2CNR'R'')_3$$

wherein R' and R'' are individually selected from the group consisting of saturated or unsaturated, substituted or unsubstituted alkyl or aryl hydrocarbon radicals containing from one to six carbon atoms inclusive.

8. The compound selected from the group consisting of those compounds set forth in claim 7 wherein R' and R'' are selected from the group consisting of methyl groups, ethyl groups and propyl groups.

9. The compound of claim 8 wherein R' and R'' are both methyl groups.

10. A compound selected from the group consisting of those compounds of the formula:

$$HSiR_2(O_2CNR'R'')_1$$

wherein R is a saturated or unsaturated, substituted or unsubstituted alkyl, aryl, alkoxy, or dialkyl amino radical containing from one to six carbon atoms inclusive; and R' and R'' are individually selected from the group consisting of saturated or unsaturated, substituted or unsubstituted alkyl or aryl hydrocarbon radicals containing from one to six carbon atoms inclusive.

11. The compound selected from the group consisting of those compounds set forth in claim 10 wherein R is an alkyl, alkoxy or dialkylamino radical containing from one to three carbon atoms inclusive and R' and R" are individually alkyl hydrocarbon radicals containing from one to three carbon atoms inclusive.

12. The compound of claim 11 wherein R is a dimethylamino group and R' and R" are both methyl group.

13. The compound of claim 11 wherein R, R' and R" are all methyl groups.

14. A compound selected from the group consisting of those compounds of the formula:

HSiR$_1$(O$_2$CNR'R")$_2$ wherein R is a saturated or unsaturated, substituted or unsubstituted alkyl, aryl, alkoxy or dialkylamino radical containing from one to six carbon atoms inclusive; and R' and R" are individually selected from the group consisting of saturated or unsaturated, substituted or unsubstituted alkyl or aryl hydrocarbon radicals containing from one to twelve carbon atoms inclusive.

15. The compound selected from the group consisting of those compounds set forth in claim 14 wherein R is an alkyl, alkoxy or dialkylamino radical containing from one to three carbon atoms inclusive and R' and R" are individually alkyl hydrocarbon radicals containing from one to three carbon atoms inclusive.

16. Tris(dimethylcarbamato)silane.
17. Bis(dimethylcarbamato)dimethylaminosilane.
18. Bis(dimethylcarbamato)methylsilane.
19. Dimethylcarbamatodimethylsilane.

* * * * *